United States Patent
Karabin et al.

(10) Patent No.: US 10,201,402 B2
(45) Date of Patent: Feb. 12, 2019

(54) ORTHODONTIC APPLIANCE AND ORTHODONTIC TREATMENT USING THE SAME

(71) Applicant: ACME MONACO CORPORATION, New Britain, CT (US)

(72) Inventors: Lucas B. Karabin, Southington, CT (US); Richard W. Selander, Terryville, CT (US); Dennis C. Lavoie, Sr., Bristol, CT (US); Diane M. Hunter, Southington, CT (US); Richard H. Ritucci, Middlebury, CT (US)

(73) Assignee: ACME MONACO CORPORATION, New Britain, CT (US)

( * ) Notice: Subject to any disclaimer, the term of this patent is extended or adjusted under 35 U.S.C. 154(b) by 0 days.

(21) Appl. No.: 15/219,325

(22) Filed: Jul. 26, 2016

(65) Prior Publication Data
US 2017/0027665 A1    Feb. 2, 2017

Related U.S. Application Data

(60) Provisional application No. 62/197,223, filed on Jul. 27, 2015.

(51) Int. Cl.
*A61C 7/28*    (2006.01)
*A61C 7/30*    (2006.01)
*A61C 7/14*    (2006.01)

(52) U.S. Cl.
CPC .............. *A61C 7/282* (2013.01); *A61C 7/148* (2013.01); *A61C 7/303* (2013.01)

(58) Field of Classification Search
CPC .......... A61C 7/282; A61C 7/148; A61C 7/303

USPC ..................................................... 433/17, 22
See application file for complete search history.

(56) References Cited

U.S. PATENT DOCUMENTS

| | | | | |
|---|---|---|---|---|
| 4,015,334 A | * | 4/1977 | Moss | A61C 7/282 433/17 |
| 4,639,219 A | * | 1/1987 | Gagin | A61C 7/12 433/22 |
| 5,306,142 A | * | 4/1994 | Richards | A61C 7/00 433/17 |
| D346,860 S | * | 5/1994 | Kesling | A61C 7/282 D24/180 |
| 6,039,564 A | * | 3/2000 | Hendrick | A61C 7/12 433/17 |

(Continued)

FOREIGN PATENT DOCUMENTS

WO    WO 2008030061 A9 *    1/2009    ........... A61C 7/12

*Primary Examiner* — Matthew Nelson
(74) *Attorney, Agent, or Firm* — Fitch, Even, Tabin & Flannery, LLP

(57) ABSTRACT

An orthodontic appliance, includes a crimpable tubular shaped portion having at least three walls selected from the group consisting of a lingual wall, a buccal or labial wall, an occlusal wall and a gingival wall, the at least three walls defining and opening configured to receive an archwire therethrough in a mesial-distal direction. The appliance includes at least one wing joined to the tubular shaped portion, the at least one wing extending longitudinally in the mesial-distal direction. A slot is provided in the at least one wing open to an end of the wing in the mesial or distal direction and having a depth in the mesial distal direction and a height in a gingival-occlusal direction configured to receive a ligature wire or elastic.

20 Claims, 7 Drawing Sheets

(56) References Cited

U.S. PATENT DOCUMENTS

| | | | | |
|---|---|---|---|---|
| 6,217,324 B1* | 4/2001 | Kesling | .................... | A61C 7/00 |
| | | | | 433/14 |
| 8,550,814 B1* | 10/2013 | Collins | .................... | A61C 7/12 |
| | | | | 433/17 |
| 2008/0286711 A1* | 11/2008 | Corcoran | ............... | A61C 7/282 |
| | | | | 433/18 |
| 2016/0302891 A1* | 10/2016 | Paehl | ........................ | A61C 7/36 |

* cited by examiner

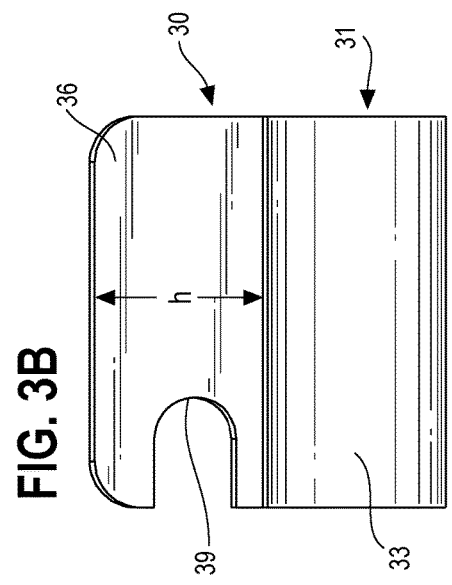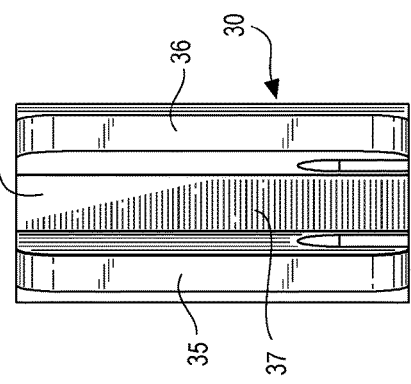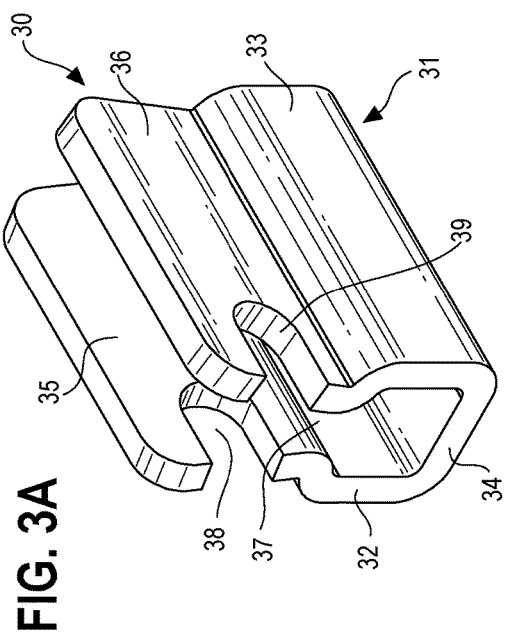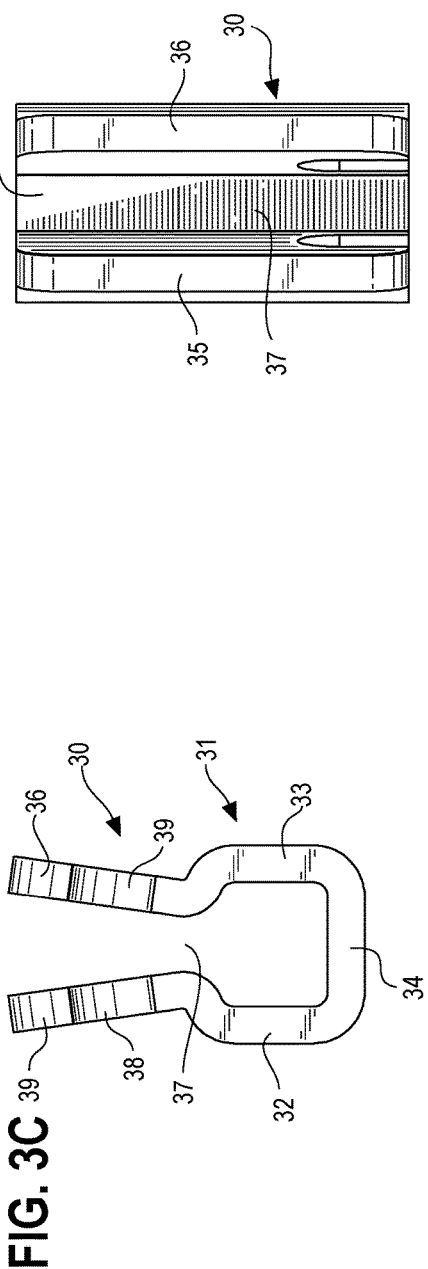

ORTHODONTIC APPLIANCE AND ORTHODONTIC TREATMENT USING THE SAME

CROSS-REFERENCE TO RELATED APPLICATION

This application is a nonprovisional application claiming benefit of the filing date of provisional application 62/197,223, filed Jul. 27, 2015, the contents of which is incorporated herein in its entirety.

BACKGROUND OF THE INVENTION

The objective of orthodontic treatment is to reconfigure teeth in a patient's mouth to achieve a comfortable, functional bite and a more attractive smile. Orthodontists use various hardware configurations commonly known as braces to achieve this. Braces primarily consist of brackets, archwires, and auxiliaries, e.g., elastics, springs, stops and tie-backs. Together, brackets, archwires, and auxiliaries enable the orthodontist to tailor movement and repositioning of individual or segments of teeth by transferring forces to the dental facial structures.

Orthodontists have used stops on archwires since the beginning of orthodontics as a specialty in the early twentieth century. A traditional use of a stop is to prevent the archwire from sliding through a bracket beyond the desired position. This situation would cause discomfort to the patient because the end of the wire would poke out beyond the bracket into the cheek. Stops had the appearance of a V-Shaped dimple and were bent in the archwire by the orthodontist. The placement of two such stops on either side of an orthodontic bracket would prevent the archwire from sliding through the brackets and thus prevent irritation of the oral soft tissues. Two stops could also be placed on the distal side of the terminal bracket on each side of a segment of teeth to prevent space from opening in that segment, for example distal to the right and left maxillary lateral incisor brackets.

Tie backs were also bent in the archwire and were a modification of a stop. A conventional tie back loop is shown in FIG. 1. A conventional tie back loop 1 bent in archwire 2 has, as shown in FIG. 1, the appearance of a tear drop and is usually placed mesial to the first molar brackets. The tie back loop 1 can be tied to the bracket 3 (to a hook 3' of the bracket) with a ligature 4 for the purpose of preventing space from opening throughout the dental arch. Tie back loops could also be placed several millimeters mesial to the first molar brackets in an archwire which also had closing loops bent in it. The tie backs could then be tied to the first molar bracket with a ligature and thereby activate the closing loops.

It is also possible to provide a tie back hook on an archwire, e.g., by soldering. A conventional tie back hook 5 is shown in FIG. 2 fixed to the archwire 2. The tie back hook 5 can be tied to the bracket 3 (to a hook 3' of the bracket) with a ligature 4 for the purpose of preventing space from opening throughout the dental arch.

The bending of stops and tie backs in an archwire is a time consuming process. The development of crimpable stops facilitated the placement of stops. An archwire could be marked with a wax marker and a small stainless steel tube could be slid on the wire to the mark and simply crimped with an orthodontic plier to secure it in place. The placement of crimpable stops serves the same functions of preventing archwires from sliding through the brackets and preventing space from opening in a segment as the stops bent in the archwire did. Conventional crimpable stops cannot be used as tie backs, however, since there is no way to tie a ligature to them.

A crimpable stop having a hook is also known. See U.S. Pat. No. 5,306,142 to Richards, the contents of which are incorporated herein by reference. The Richards patent discloses an orthodontic device defining an anchor for an elastic, ligature or spring. It combines a ball hook attached to a crimpable stop, the stop having a tubular body with inner wire-engaging surfaces coated with an abrasive material to produce an anti-sliding and anti-rotating engagement with the wire when crimped down upon the wire. This patent discloses that the crimpable ball hooks can be mounted on archwires and when used with intermaxillary elastics can provide intermaxillary fixation, can be mounted on a lip bumper received in buccal tubes or can be mounted on the inner bow of a face bow received in buccal tubes. The hooks tend to be large, e.g., have a height of about 4 mm in the gingival-occlusal direction and can cause irritation of the gingiva.

SUMMARY OF THE INVENTION

The present invention relates to an orthodontic appliance, including a crimpable tubular shaped portion having at least three walls selected from the group consisting of a lingual wall, a buccal or labial wall, an occlusal wall and a gingival wall, the at least three walls defining an opening configured to receive an archwire therethrough in a mesial-distal direction. The appliance includes at least one wing joined to the tubular shaped portion, the at least one wing extending longitudinally in the mesial-distal direction. A slot is provided in the at least one wing open to an end of the wing in the mesial or distal direction and having a depth in the mesial distal direction and a height in a gingival-occlusal direction configured to receive a ligature wire or elastic.

BRIEF DESCRIPTION OF THE DRAWINGS

FIG. 3A is a schematic perspective view of one embodiment of an orthodontic appliance according to the present invention.

FIG. 3B is a schematic front view of the orthodontic appliance of FIG. 3A.

FIG. 3C is a schematic left end view of the orthodontic appliance of FIG. 3A.

FIG. 3D is a schematic top view of the orthodontic appliance of FIG. 3A.

DETAILED DESCRIPTION OF THE PREFERRED EMBODIMENTS

Figure 1:
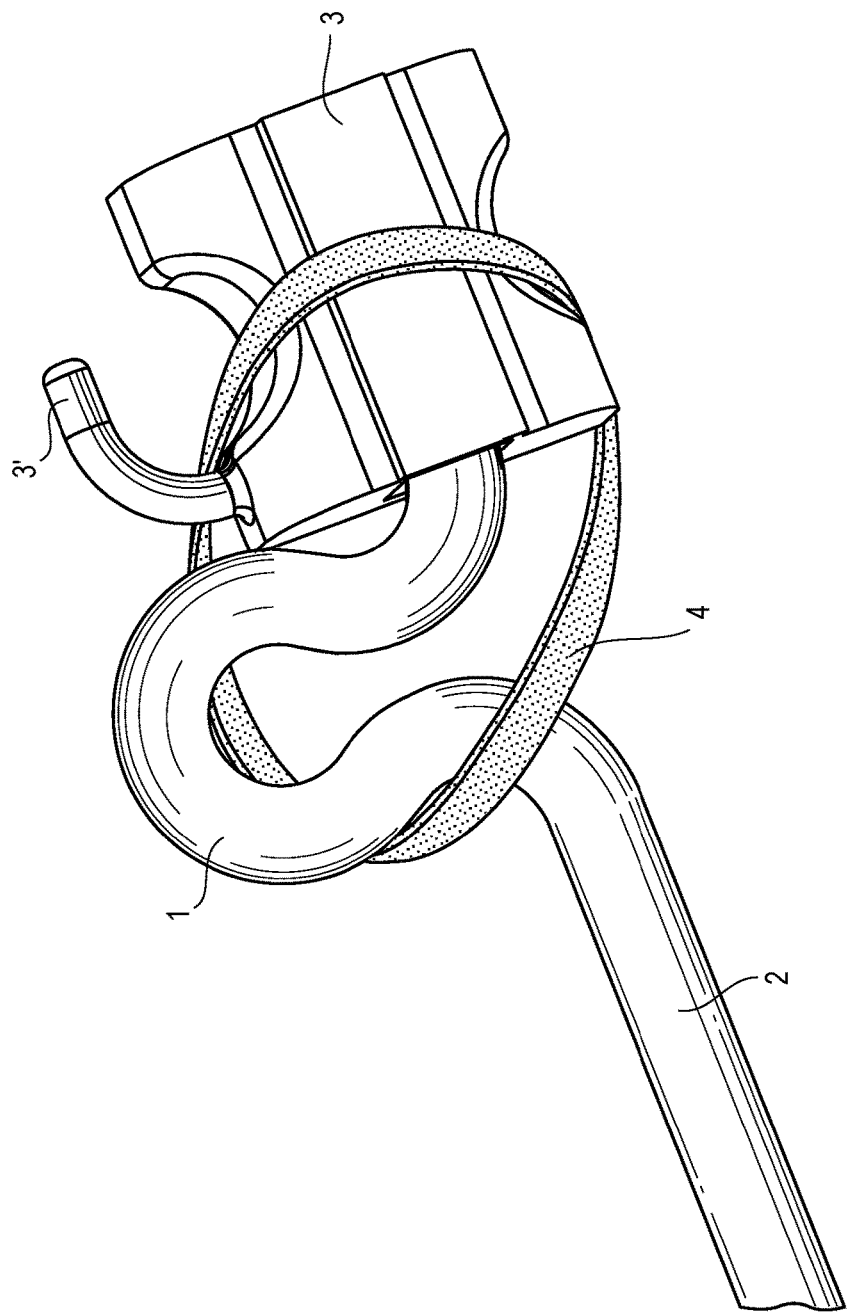
FIG. 1 is a schematic view of a conventional tie back loop.
Figure 2:
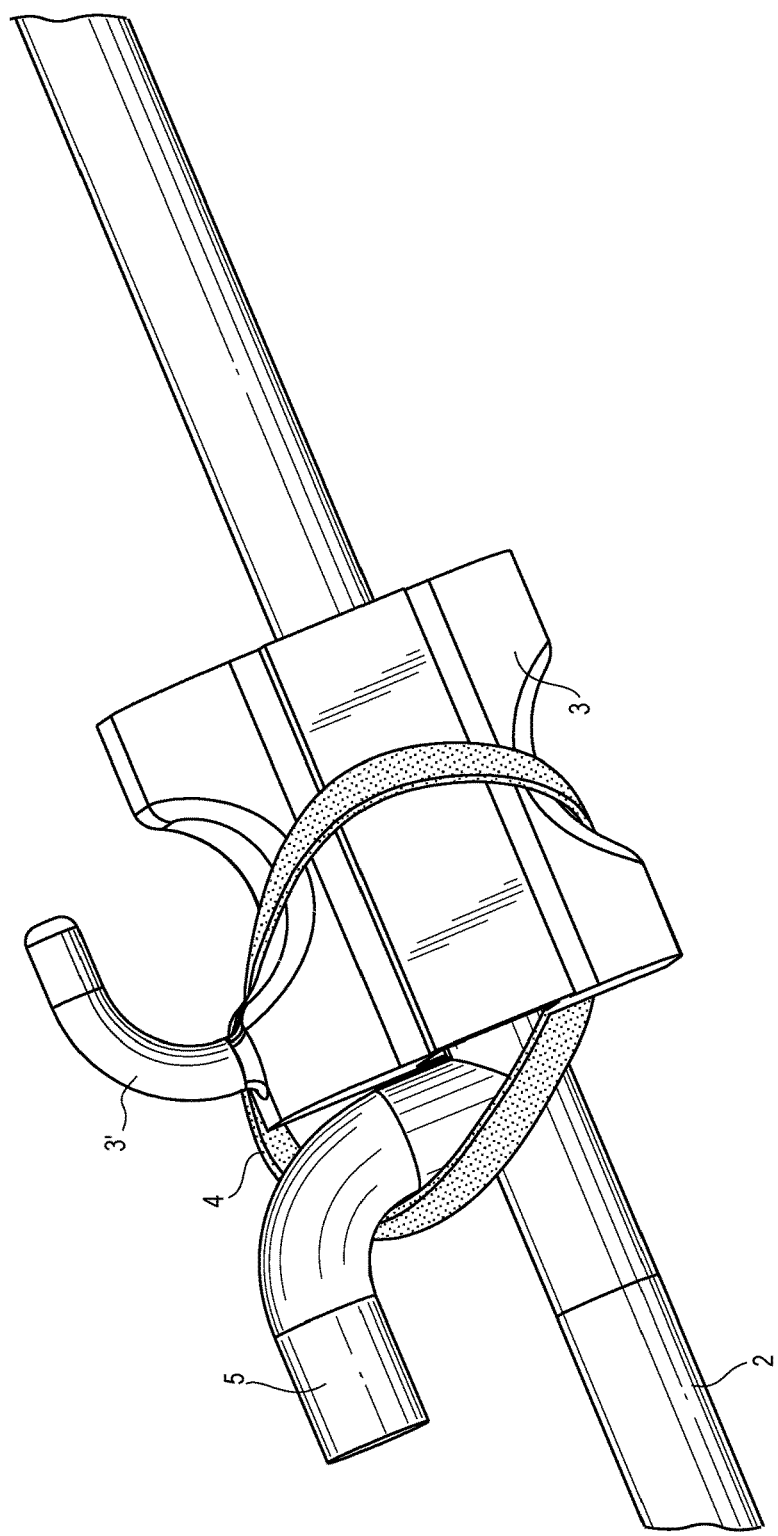
FIG. 2 is a schematic view of a conventional tie back hook.

Applicant has developed an orthodontic appliance that is a modification of the crimpable stop to allow it to also be used as a tie back. The modified crimpable stop of the present invention includes a slot incorporated in a portion of the stop, the slot being configured to allow the placement of a ligature, e.g., made of stainless steel, which then allows the modified crimpable stop to function in the same way as the tie back bent in the archwire would, i.e., preventing space from opening throughout the dental arch. In a preferred embodiment, the slot has the dimensions 0.018×0.015 inch to allow the placement of the ligature. The same benefit of ease of placement as the conventional crimpable stop applies as well as the benefit of the modified crimpable stop being much smaller than a tie back bent in the archwire and having a shorter height in the gingival-occlusal direction, and therefore much less likely to cause irritation of the oral soft tissues as well as being more hygienic.

FIGS. 3A-3D are schematic views showing one embodiment of an orthodontic appliance, in the form of a modified crimpable stop, according to the present invention. FIG. 3A is a schematic perspective view of one embodiment of an orthodontic appliance according to the present invention. FIG. 3B is a schematic front view of the orthodontic appliance of FIG. 3A. FIG. 3C is a schematic left end view of the orthodontic appliance of FIG. 3A. FIG. 3D is a schematic top view of the orthodontic appliance of FIG. 3A. The internal lines in the drawings are intended to show changes in direction/elevation and not intended to depict that the stop is made of separate pieces. In fact, it is preferred that the stop is made as a single unitary piece of orthodontic-grade corrosion-resistant material, such as stainless steel, by, e.g., stamping, molding or forming.

FIGS. 3A-3D show the orthodontic appliance, in the form of a modified crimpable stop, generally designated by the reference numeral 30, according to one embodiment of the present invention. The crimpable stop 30 has a tubular shaped portion 31 having, in this embodiment, a generally rectangular inner cross-section or profile defining a tubular opening configured to receive an archwire therethrough. The tubular shaped portion 31 has a lingual wall 32 opposed to a buccal (or labial) wall 33 joined by an occlusal wall 34. The tubular shaped portion 31 is joined to a pair of extensions or wings 35 and 36. The lower portions of the extensions or wings 35 and 36, where they join, respectively, the lingual wall 32 and buccal (or labial) wall 33, forms a partial gingival wall having an opening 37. This opening 37 allows the crimpable stop 30 to be placed on the archwire, even if the archwire is already attached to the brackets in a patient's mouth. The tubular shaped portion 31 has a length in the mesial-distal direction long enough for the wings to provide sufficient strength for the ligature in the slots and short enough so as not to completely occupy the interbracket distance, e.g., a length of about 1.5 mm to 2.5 mm, preferably 2.16 mm in the mesial-distal direction. Preferably, the extensions or wings 35 and 36 preferably have a length in the mesial-distal direction the same as the length of the tubular shaped portion 31 in the mesial-distal direction or slightly shorter as long as the wings are long enough for the wings to provide sufficient strength for the ligature in the slots. The extensions or wings 35 and 36 have a height h (see FIG. 3B) in the gingival-occlusal direction as short as possible but still have sufficient strength for the ligature in the slots, e.g., about 0.7 to 2.5 mm, preferably, 0.9 to 1.1 mm, e.g., about 1 mm.

The extensions or wings 35 and 36 have slots 38 and 39, respectively, provided therein. The slots 38, 39 are configured to allow the placement of a ligature, e.g., made of stainless steel, which then allows the modified crimpable stop 30 to function in the same way as the tie back bent in the archwire would, i.e., preventing space from opening throughout the dental arch. In a preferred embodiment, each of the slots 38, 39 has the dimensions 0.01 inch to 0.05 inch, e.g., 0.024 inch (depth in the mesial-distal direction) x 0.01 to 0.02, e.g., 0.018 inch (height in the gingival-occlusal direction) to allow the placement of the ligature. Each slot 38, 39 opens at one end in the mesial-distal direction, is closed at the other end in the mesial-distal direction and is closed in the gingival and occlusal directions. In the embodiment shown in the drawings, the slot 38, 39 has a C or inverted C shape. Of course, other shapes for the slot (e.g., a V-shape rotated by, e.g., 90°) can be used as long as the slots are configured to allow the placement of a ligature as will be described in more detail hereinafter. If it is desired to use an elastic rather than a stainless steel ligature in the slot, the slot can be sized accordingly (e.g., having a depth in the mesial-distal direction and a height in the gingival-occlusal direction) to match the diameter of the elastic (e.g., 0.028 inch). However, since the elastic is soft and will narrow when stretched, the size of the slot can be smaller than the diameter of the elastic and the elastic can still fit within the slot.

Figure 3F:
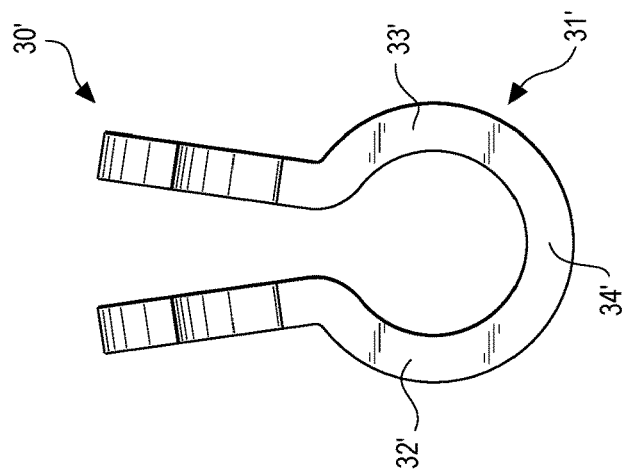
FIG. 3F is a schematic left end view of the orthodontic appliance of FIG. 3E.
Figure 3E:
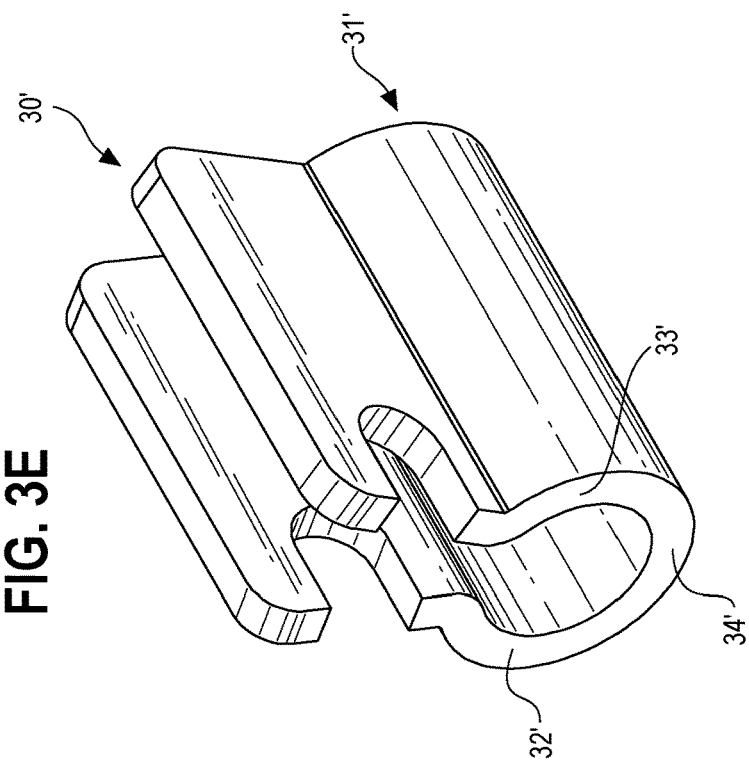
FIG. 3E is a schematic perspective view of another embodiment of an orthodontic appliance according to the present invention.

FIG. 3E is a schematic perspective view of another embodiment of an orthodontic appliance according to the present invention and FIG. 3F is a schematic left end view of the orthodontic appliance of FIG. 3E. The embodiment of FIGS. 3E and 3F is similar to that of FIGS. 3A-3D but is specifically made for use with a round archwire as will be explained below. In this embodiment, the tubular shaped portion 31' has a semicircular cross-sectional profile with a lingual wall 32' opposed to a buccal (or labial) wall 33' joined by an occlusal wall 34'.

Figure 4A:
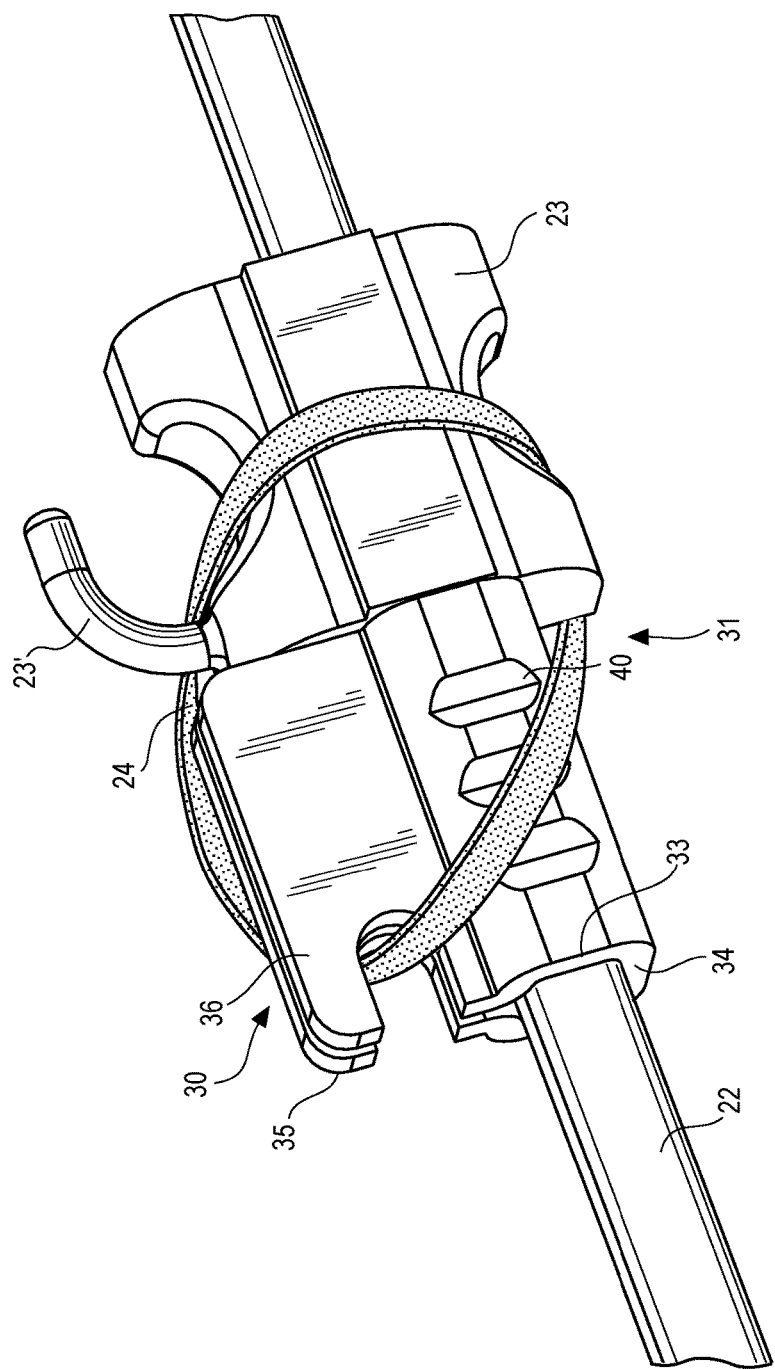
FIG. 4A is a schematic view of an embodiment of the orthodontic appliance of the present invention in use in an orthodontic treatment using a rectangular archwire.

FIG. 4A is a schematic view of an embodiment of the orthodontic appliance 30 of the present invention in use in an orthodontic treatment using a rectangular archwire 22. In FIG. 4A, the crimpable stop 30 has been placed on the archwire and crimped, the crimping taking place in a manner known in the art to fix the stop 30 on the archwire 22. For example, orthodontic ligature cutters can be used to crimp the stop 30 onto the archwire 22 so that the stop 30 is fixed in place on the archwire 22 by friction and/or forming indentations in the stop 30 and archwire 22. In FIG. 4A, the marks or indentations made by the ligature cutter are shown with reference numeral 40. It is also possible to crimp the wings 35, 36. A friction increasing coating or surface, such as diamond grit, can be provided on the inner walls of the tubular shaped portion 31 to provide an anti-sliding effect. The opening 37 allows the crimpable stop 30 to be placed on the archwire 22, even if the archwire is already attached to the brackets 23 in a patient's mouth. It is also possible to slip the archwire 22 through the tubular shaped portion 31 before the archwire 22 is attached to the brackets 23 in a patient's mouth. In this latter case, it is possible to make the tubular shaped portion 31 such that there is a complete gingival wall, i.e., one not having an opening 37.

Once the stop 30 is crimped onto the archwire 22, the orthodontist or technician can tie it off with ligature wire 24, e.g., in a figure-eight configuration, to secure the stop 30 to an anchor point such as a hook 23' on bracket 23, or to activate a closing loop. Alternatively, an elastic ligature can be used.

Figure 4B:
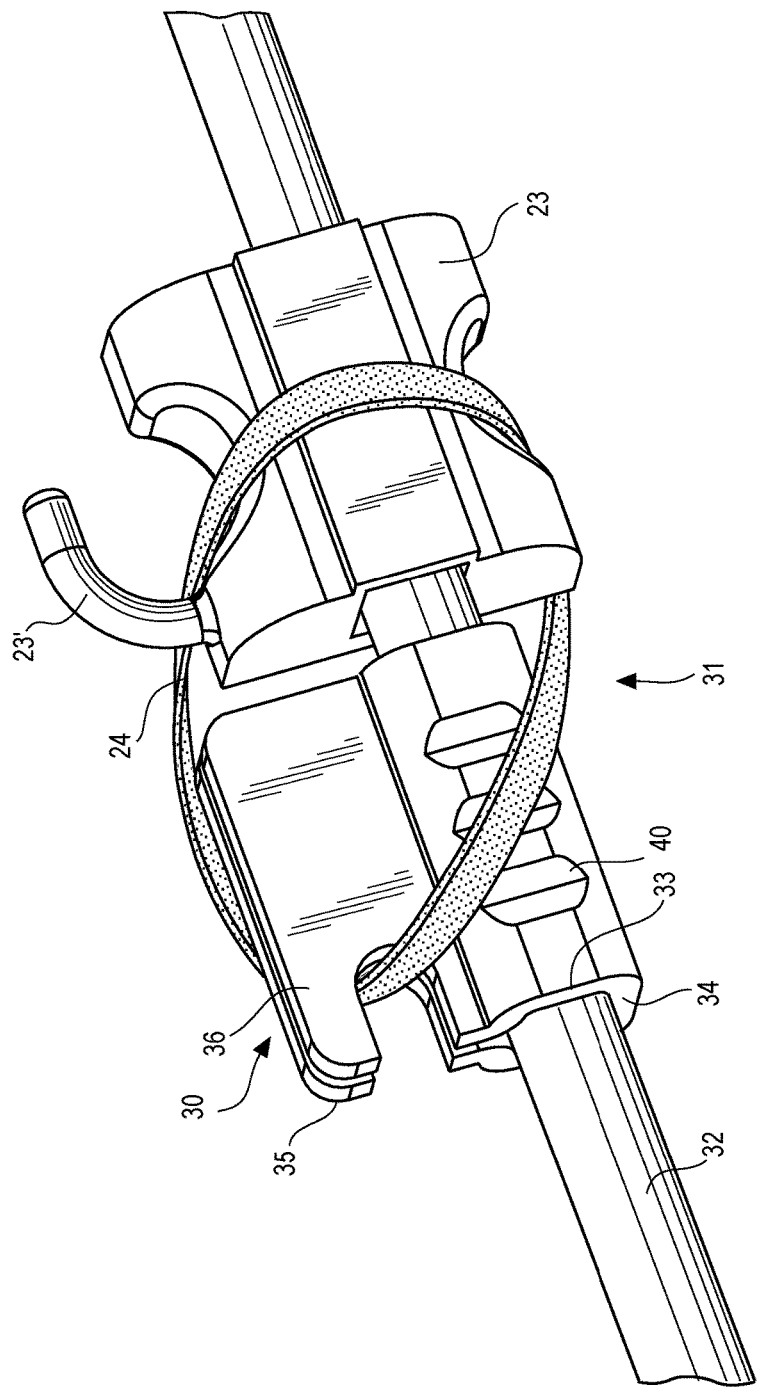
FIG. 4B is a schematic view of an embodiment of the orthodontic appliance of the present invention in use in an orthodontic treatment using a round archwire.
Figure 4C:
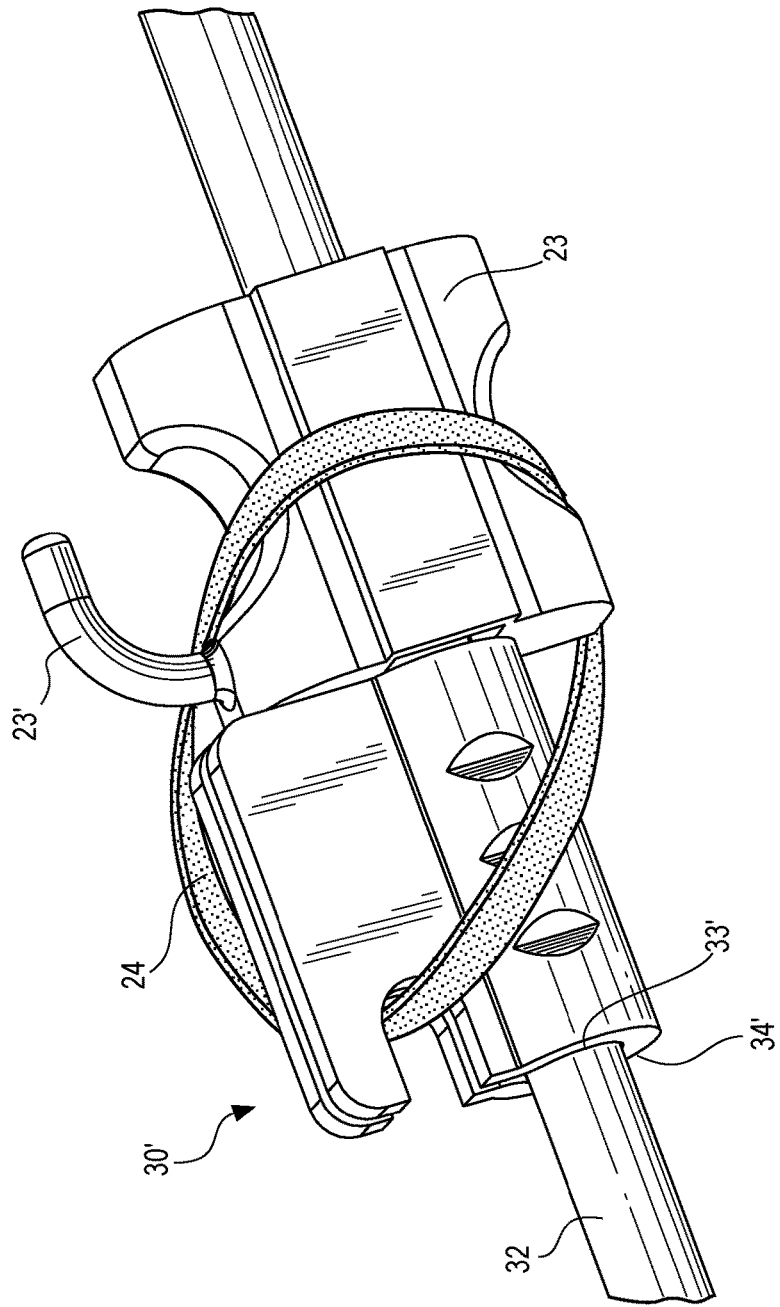
FIG. 4C is a schematic view of another embodiment of the orthodontic appliance of the present invention in use in an orthodontic treatment using a round archwire.

FIG. 4B is a schematic view of an embodiment of the orthodontic appliance 30 of the present invention in use in an orthodontic treatment using a round archwire 32. In this case, a tubular shaped portion 31 having a generally rectangular inner cross-section or profile may be used if there is sufficient friction. Preferably, however, as shown in FIGS. 3E, 3F and 4C, the tubular shaped portion 31' will have a generally semicircular or circular inner cross-section or profile, the diameter of which would preferably be 0.165 inch-0.19 inch, e.g., 0.17 for 0.16 archwires and 0.19 for 0.18 archwires. FIG. 4C is a schematic view of this embodiment of the orthodontic appliance 30' of the present invention in use in an orthodontic treatment using a round archwire 32.

While the orthodontic appliance of the present invention can be used anywhere in the patient's mouth as desired by the orthodontist, it is especially advantageous for use between the second pre-molars and the first molars or between the first molars and the second molars. The present invention provides advantages over the prior art, including being more hygienic, having a small height in the gingival-occlusal direction providing less irritation and more comfort, and having a small length in mesial-distal greater providing a great range of activation.

While one orientation of the stop 30 has been shown in the FIGS. 3A-3D, 4A and 4B, it is possible, of course, to use the stop 30 rotated 180° in the horizontal plane (about a vertical axis), in which case, the wall 32 would be a buccal (or labial) wall and the wall 33 a lingual wall. Alternatively or additionally, the stop 30 rotated 180° in the vertical plane (about a horizontal axis), in which case wall 34 would be a gingival wall and the portions of the extensions or wings 35 and 36 that join the lingual wall and buccal (or labial) wall would form a partial occlusal wall.

What is claimed is:

1. An orthodontic appliance, comprising:
   a crimpable tubular shaped portion having at least three walls selected from the group consisting of a lingual wall, a buccal or labial wall, an occlusal wall and a gingival wall, the at least three walls defining an opening configured to receive an archwire therethrough in a mesial-distal direction;
   a pair of wings joined to the tubular shaped portion, each of the pair of wings extending longitudinally in the mesial-distal direction and being separated from one another by a space continuous with the opening that allows the appliance to be placed on the archwire even if the archwire is attached to brackets in a patient's mouth, wherein each of the pair of wings has a length in the mesial-distal direction substantially the same as a length of the tubular shaped portion in the mesial-distal direction; and
   a slot provided in each of the pair of wings open to an end of the wing in the mesial or distal direction and having a depth in the mesial distal direction and a height in a gingival-occlusal direction configured to receive a ligature wire or elastic.

2. The orthodontic appliance according to claim 1, wherein each of the pair of wings has a height in the gingival-occlusal direction of 2.5 mm or less.

3. The orthodontic appliance according to claim 1, wherein each of the pair of wings has a height in the gingival-occlusal direction in a range of 0.7 to 2.5 mm.

4. The orthodontic appliance according to claim 1, wherein each of the pair of wings has a height in the gingival-occlusal direction in a range of 0.9 to 1.1 mm.

5. The orthodontic appliance according to claim 1, wherein the slot is provided in each of the pair of wings within a distance in the gingival-occlusal direction of less than 2.5 mm from the tubular shaped portion.

6. The orthodontic appliance according to claim 1, wherein the tubular shaped portion has a length in the mesial-distal direction of 2.5 mm or less.

7. The orthodontic appliance according to claim 1, wherein the tubular shaped portion has a length in the mesial-distal direction in a range of 1.5 mm to 2.5 mm.

8. The orthodontic appliance according to claim 1, wherein inner walls of the tubular shaped portion defining the opening in the tubular shaped portion are provided with a friction increasing coating or surface.

9. The orthodontic appliance according to claim 1, wherein inner walls of the tubular shaped portion defining the opening in the tubular shaped portion are provided with a diamond grit coating.

10. An orthodontic appliance, comprising:
    a crimpable tubular shaped portion having at least three walls selected from the group consisting of a lingual wall, a buccal or labial wall, an occlusal wall and a gingival wall, the at least three walls defining an opening configured to receive an archwire therethrough in a mesial-distal direction, wherein the tubular shaped portion has a length in the mesial-distal direction of 2.5 mm or less;
    a pair of wings joined to the tubular shaped portion, each of the pair of wings extending longitudinally in the mesial-distal direction and being separated from one another by a space continuous with the opening that allows the appliance to be placed on the archwire even if the archwire is attached to brackets in a patient's mouth; and
    a slot provided in each of the pair of wings open to an end of the wing in the mesial or distal direction and having a depth in the mesial distal direction and a height in a gingival-occlusal direction configured to receive a ligature wire or elastic.

11. The orthodontic appliance according to claim 10, wherein each of the pair of wings has a height in the gingival-occlusal direction of 2.5 mm or less.

12. The orthodontic appliance according to claim 10, wherein each of the pair of wings has a height in the gingival-occlusal direction in a range of 0.7 to 2.5 mm.

13. The orthodontic appliance according to claim 10, wherein each of the pair of wings has a height in the gingival-occlusal direction in a range of 0.9 to 1.1 mm.

14. The orthodontic appliance according to claim 10, wherein the slot is provided in each of the pair of wings within a distance in the gingival-occlusal direction of less than 2.5 mm from the tubular shaped portion.

15. The orthodontic appliance according to claim 10, wherein the tubular shaped portion has a length in the mesial-distal direction in a range of 1.5 mm to 2.5 mm.

16. The orthodontic appliance according to claim 10, wherein inner walls of the tubular shaped portion defining the opening in the tubular shaped portion are provided with a friction increasing coating or surface.

17. The orthodontic appliance according to claim 10, wherein inner walls of the tubular shaped portion defining the opening in the tubular shaped portion are provided with a diamond grit coating.

18. An orthodontic appliance, comprising:
    a crimpable tubular shaped portion having at least three walls selected from the group consisting of a lingual wall, a buccal or labial wall, an occlusal wall and a gingival wall, the at least three walls defining an opening configured to receive an archwire therethrough in a mesial-distal direction;

a pair of wings joined to the tubular shaped portion, each of the pair of wings extending longitudinally in the mesial-distal direction and being separated from one another by a space continuous with the opening that allows the appliance to be placed on the archwire even if the archwire is attached to brackets in a patient's mouth; and a slot provided in each of the pair of wings open to an end of the wing in the mesial or distal direction and having a depth in the mesial distal direction and a height in a gingival-occlusal direction configured to receive a ligature wire or elastic, wherein the slot is provided in each of the pair of wings within a distance in the gingival-occlusal direction of less than 2.5 mm from the tubular shaped portion.

19. The orthodontic appliance according to claim 18, wherein inner walls of the tubular shaped portion defining the opening in the tubular shaped portion are provided with a friction increasing coating or surface.

20. The orthodontic appliance according to claim 18, wherein inner walls of the tubular shaped portion defining the opening in the tubular shaped portion are provided with a diamond grit coating.

\* \* \* \* \*